US00PP33067P2

(12) United States Plant Patent
Sills et al.

(10) Patent No.: US PP33,067 P2
(45) Date of Patent: May 18, 2021

(54) BLACKBERRY PLANT VARIETY NAMED 'DRISBLACKTWENTYTHREE'

(50) Latin Name: ***Rubus* L. subgenus *Rubus***
Varietal Denomination: DrisBlackTwentyThree

(71) Applicant: Driscoll's, Inc., Watsonville, CA (US)

(72) Inventors: Gavin R. Sills, Watsonville, CA (US); Yunwen Wang, Watsonville, CA (US); Mark F. Crusha, Watsonville, CA (US); John Fangary, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 16/602,975

(22) Filed: Jan. 8, 2020

(51) Int. Cl.
*A01H 5/08* (2018.01)
*A01H 6/74* (2018.01)

(52) U.S. Cl.
USPC ..... Plt./203

(58) Field of Classification Search
USPC ..... Plt./203
CPC ... A01H 5/08; A01H 5/00; A01H 6/74; A01H 6/7499
See application file for complete search history.

(56) References Cited

U.S. PATENT DOCUMENTS

| | | | |
|---|---|---|---|
| PP6,679 | P | 3/1989 | Moore |
| PP6,782 | P | 5/1989 | Jennings |
| PP13,525 | P3 | 1/2003 | Fear |
| PP13,758 | P3 | 5/2003 | Fear |
| PP13,759 | P3 | 5/2003 | Fear |
| PP14,682 | P3 | 4/2004 | Fear |
| PP14,765 | P2 | 5/2004 | Fear et al. |
| PP14,780 | P2 | 5/2004 | Fear et al. |
| PP15,058 | P2 | 8/2004 | Fear et al. |
| PP17,162 | P3 | 10/2006 | Clark et al. |
| PP17,983 | P2 | 9/2007 | Cabrera Avalos |
| PP22,002 | P2 | 7/2011 | Sills et al. |
| PP22,449 | P3 | 1/2012 | Clark |
| PP23,497 | P3 | 3/2013 | Clark et al. |
| PP23,725 | P3 | 7/2013 | Sills et al. |
| PP24,249 | P3 | 2/2014 | Clark |
| PP24,609 | P3 | 7/2014 | Sills et al. |
| PP24,701 | P3 | 7/2014 | Sills et al. |
| PP24,878 | P2 | 9/2014 | Sills et al. |
| PP25,502 | P3 | 5/2015 | Sills et al. |
| PP26,501 | P3 | 3/2016 | Sills et al. |
| PP26,611 | P3 | 4/2016 | Sills et al. |
| PP26,774 | P3 | 5/2016 | Sills et al. |
| PP27,129 | P2 | 9/2016 | Sills et al. |
| PP27,130 | P2 | 9/2016 | Sills et al. |
| PP27,146 | P2 | 9/2016 | Sills et al. |
| PP27,681 | P3 | 2/2017 | Sills et al. |
| PP27,746 | P3 | 3/2017 | Sills et al. |
| PP28,548 | P2 | 10/2017 | Sills et al. |
| PP31,110 | P2 | 11/2019 | Sills et al. |
| PP31,291 | P2 | 12/2019 | Sills et al. |
| 2016/0249505 | P1 | 8/2016 | Sills et al. |

OTHER PUBLICATIONS

Sills et al., Unpublished U.S. Appl. No. 16/602,974, filed Jan. 8, 2020, titled "Blackberry Plant Variety Named 'DrisBlackTwentyFour'".
Sills et al., Unpublished U.S. Appl. No. 16/602,976, filed Jan. 8, 2020, titled "Blackberry Plant Variety Named 'DrisBlackTwentyTwo'".
Sills et al., Unpublished U.S. Appl. No. 16/501,447, filed Apr. 17, 2019, titled "Blackberry Plant Variety Named 'DrisBlackTwenty'".
Sills et al., Unpublished U.S. Appl. No. 16/501,448, filed Apr. 17, 2019, titled "Blackberry Plant Variety Named 'DrisBlackNineteen'".
Sills et al., Unpublished U.S. Appl. No. 16/501,772, filed Jun. 5, 2019, titled "Blackberry Plant Variety Named 'DrisBlackTwentyOne'".
Voss, Donald H. "The Royal Horticultural Society Colour Chart 2001", Journal American Rhododendron Society, vol. 56, No. 1, 2002, 3 pages.
Williams et al., "DNA Polymorphisms Amplified by Arbitrary Primers are useful as Genetic Markers", Nucleic Acids Research, vol. 18, No. 22, 1990, pp. 6531-6535.

*Primary Examiner* — June Hwu
(74) *Attorney, Agent, or Firm* — Morrison & Foerster LLP

(57) ABSTRACT

A new and distinct variety of blackberry plant named 'DrisBlackTwentyThree', selected for the size, firmness, and flavor of the fruit, as well as the spinelessness of the plant, is disclosed.

4 Drawing Sheets

Latin name: Botanical classification: *Rubus* L. subgenus *Rubus*.

Varietal denomination: The varietal denomination of the claimed variety of blackberry plant is 'DrisBlackTwentyThree'.

BACKGROUND OF THE INVENTION

Blackberry is the common name for a multitude of plant species bearing dark purple to black aggregate fruit in the genus *Rubus* of the family Rosaceae. Most blackberries are within the subgenus *Rubus*.

Native chiefly to the northern temperate regions, blackberries are now being cultivated as a valuable fruit crop in many areas of the world, particularly in Europe, North America and Central America, Recognized for their high contents of antioxidants, dietary fiber, vitamin C, and vitamin K. Blackberry fruit are typically consumed as fresh fruit, individually quick frozen fruit, or in prepared foods, such as purées, juices, jellies, jams, grocery items, baked goods, and snack foods.

Globally, Mexico is the leading producer of blackberries, with nearly the entire crop being produced for export into the off-season fresh markets in North America and Europe. The Mexican market is almost entirely from the cultivar 'Tupi' (also spelled as 'Tupy'), In the United States, Oregon is the leading commercial blackberry producer, followed by the state of California.

Blackberries are perennial plants that typically bear biennial stems (known as "canes") from a perennial root system. The two cane types are primocanes, or first-year canes, which are usually vegetative, and floricanes, which are the same canes and produce fruit in the next growing season. In its first year, a new cane, the primocane, grows vigorously to its full length of three to six meters in a growth habit of erecting, arching, or trailing along the ground and bearing large compound leaves with 3, 5, or 7 leaflets; it does not produce any flowers. In its second year, the cane becomes a floricane and stops elongating, but the lateral buds break to produce flowering laterals that bear fruit.

Recently, primocane-fruiting blackberry varieties have been developed that are capable of flowering and fruiting on first-year canes. Primocane-fruiting blackberry varieties have several advantages, including potential of two crops on the same plant in the same year, reduction in pruning costs by mowing of canes, avoidance of winter injury, and production of fruit in an extended geographic area. However, primocane-fruiting blackberry varieties are also subject to a number of challenges, such as poor heat tolerance, lesser fruit quality, and low yield.

Blackberry is an important and valuable commercial fruit crop. Accordingly, there is a need for new varieties of blackberry plant. In particular, there is a need for improved varieties of blackberry plant that are stable, high yielding, and agronomically sound.

SUMMARY OF THE INVENTION

In order to meet these needs, the present invention is directed to an improved variety of blackberry plant. In particular, the invention relates to a new and distinct variety of blackberry plant (*Rubus* L. subgenus *Rubus*), which has been denominated as 'DrisBlackTwentyThree'.

Blackberry plant variety 'DrisBlackTwentyThree' was discovered in Santa Cruz, Calif. in July of 2012 and originated from a cross between the female parent blackberry plant 'BN864.2' (unpatented) and the male parent blackberry plant 'DrisBlackEighteen' (U.S. Plant Pat. No. 31,110). The original seedling of the new variety was first asexually propagated via root cuttings in Santa Cruz, Calif. in October of 2012.

'DrisBlackTwentyThree' was subsequently asexually propagated via root cuttings, and underwent testing in Santa Cruz, Calif. from 2014 to 2019 (five years). The present variety has been found to be stable and reproduce true to type through successive asexual propagations via root cuttings.

'DrisBlackTwentyThree' exhibits the following distinguishing characteristics over other similar varieties when grown under normal horticultural practices in Santa Cruz, Calif.:

1. Upright growth habit;
2. Medium anthocyanin coloration during rapid growth on young shoot;
3. White petal color; and
4. Elliptic fruit shape in longitudinal section.

'DrisBlackTwentyThree' was selected for the size, firmness, and flavor of the fruit, as well as the spinelessness of the plant.

BRIEF DESCRIPTION OF THE DRAWINGS

This new blackberry plant is illustrated by the accompanying photographs. The colors shown are as true as can be reasonably obtained by conventional photographic procedures. The photographs are of plants that are two to five years old.

DETAILED BOTANICAL DESCRIPTION

Figure 1:
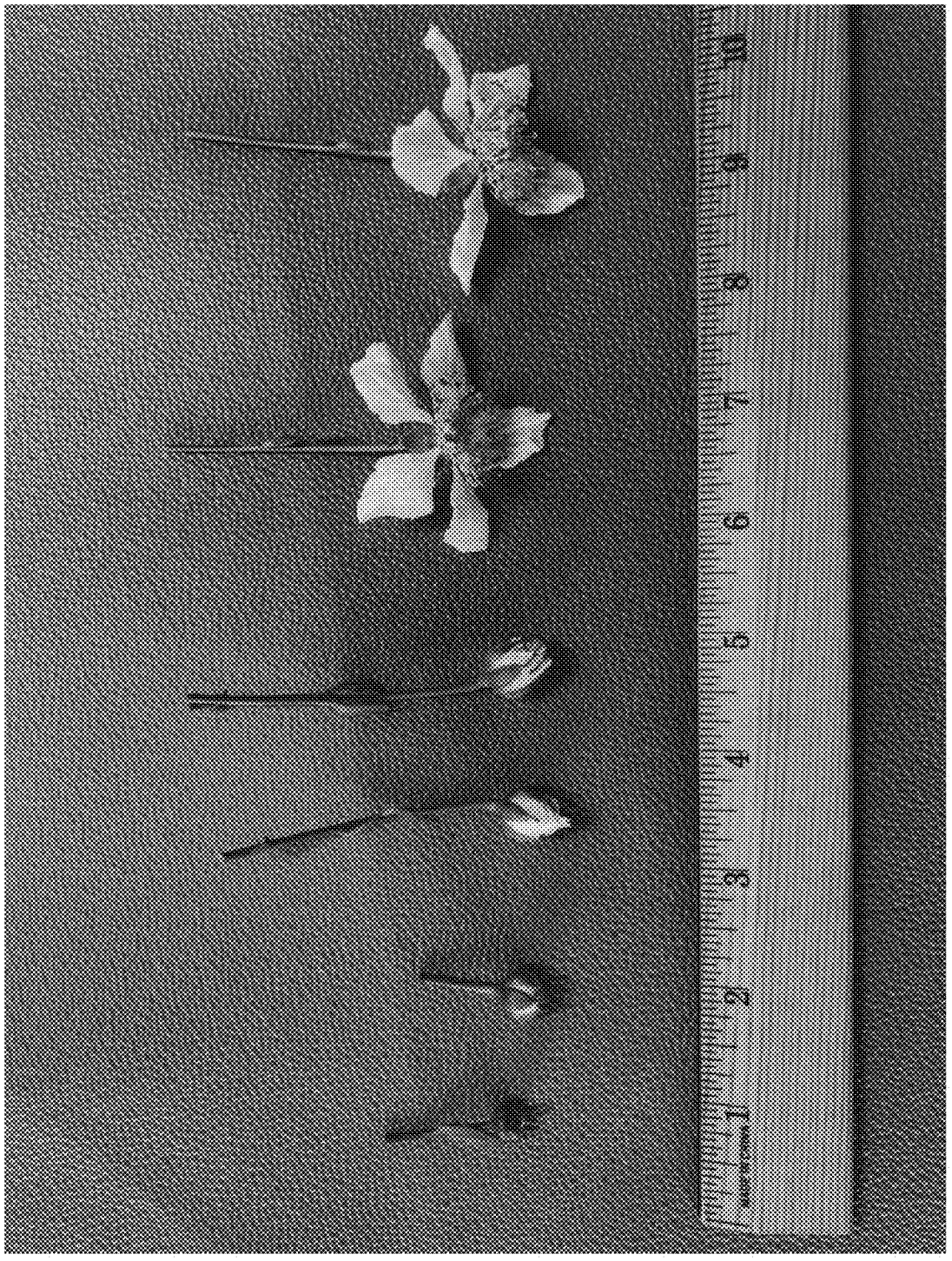
FIG. 1 illustrates flowers of variety 'DrisBlackTwentyThree' at various stages of development.
Figure 2:
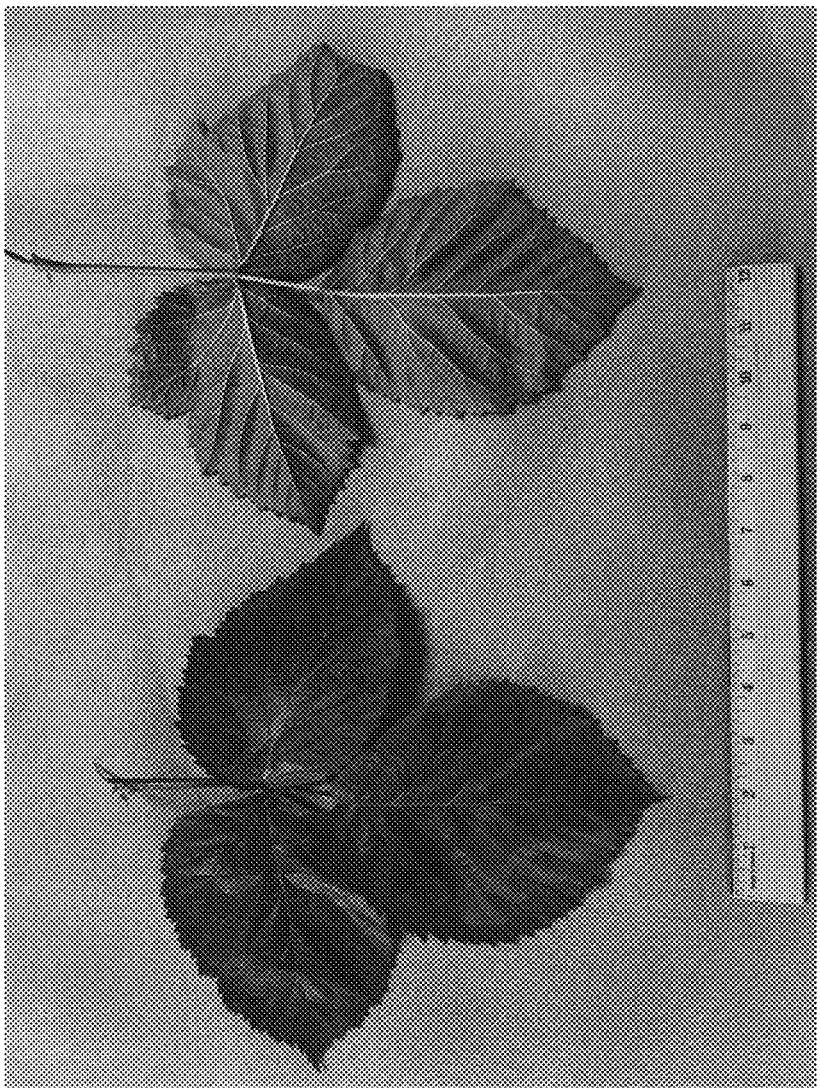
FIG. 2 illustrates leaves of variety 'DrisBlackTwentyThree'. The upper side of a leaf is shown on the left, and the lower side of a leaf is shown on the right.
Figure 3:
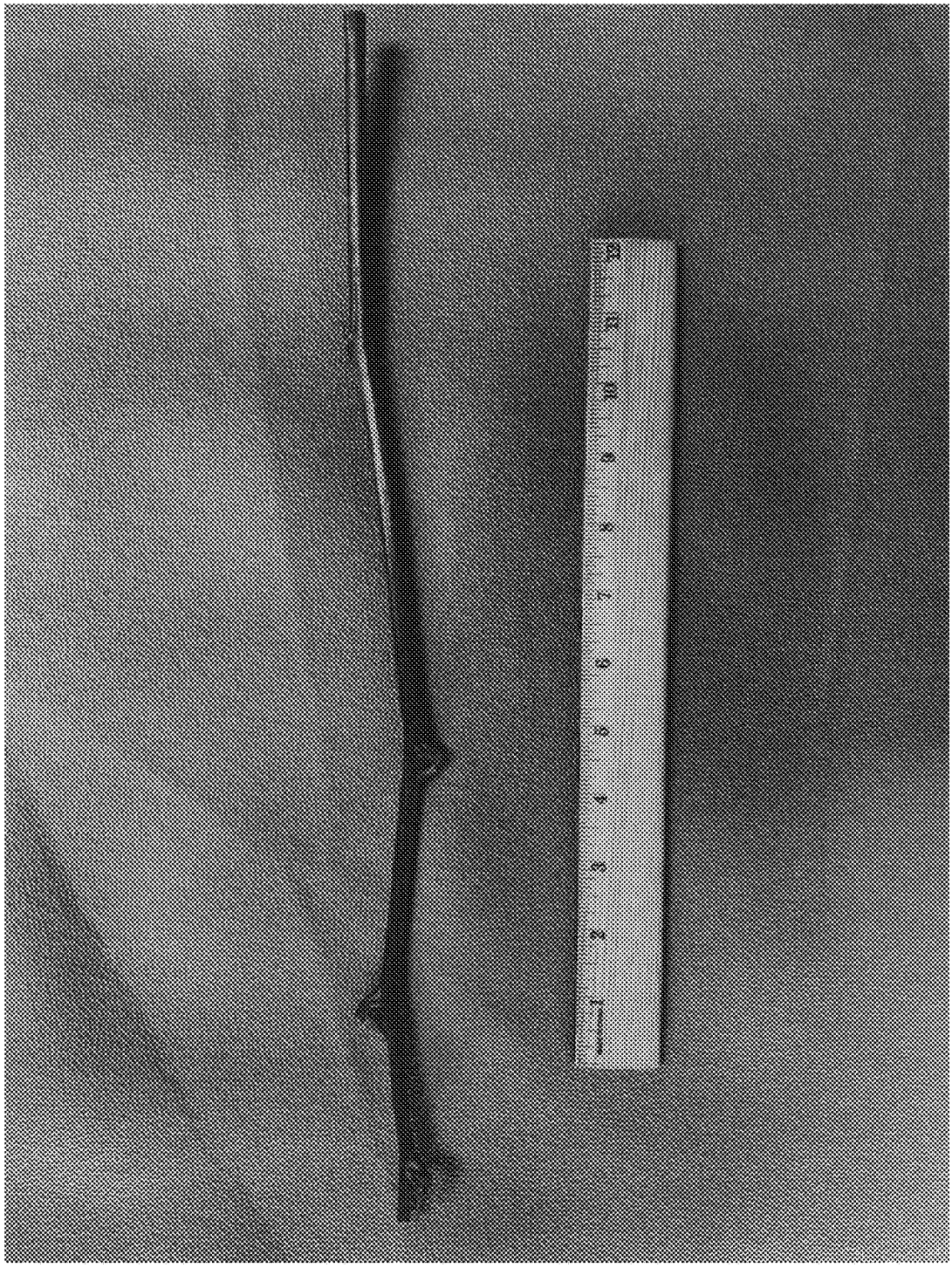
FIG. 3 illustrates a section of a cane of variety 'DrisBlackTwentyThree'.
Figure 4:
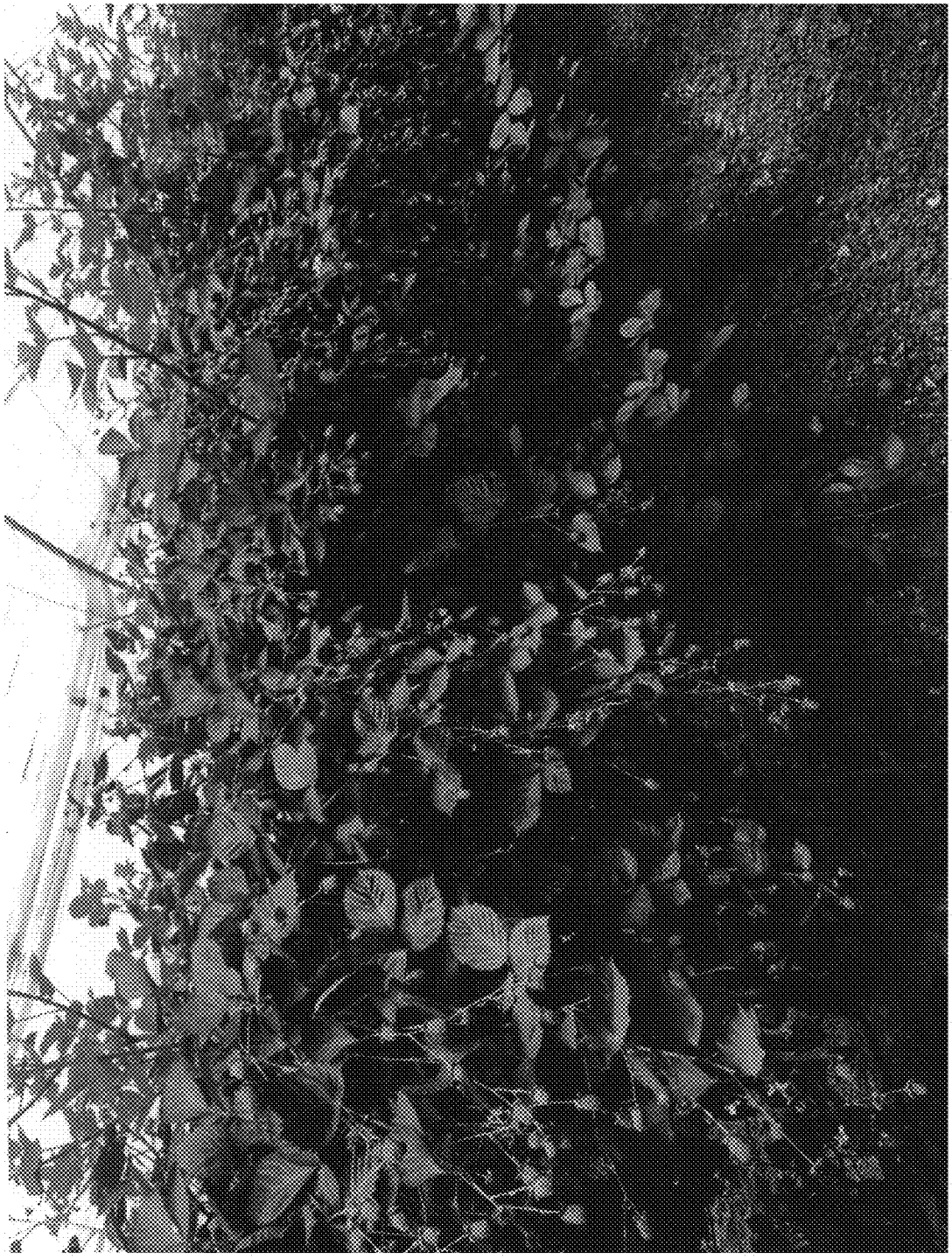
FIG. 4 illustrates plants of variety 'DrisBlackTwentyThree' bearing fruit at various developmental stages.

The following descriptions set forth the distinctive characteristics of 'DrisBlackTwentyThree'. The data that define these characteristics are based on observations taken in Santa Cruz, Calif. from 2014 to 2019. This description is in accordance with UPOV terminology. Color designations, color descriptions, and other phenotypical descriptions may deviate from the stated values and descriptions depending upon variation in environmental, seasonal, climatic and cultural conditions. 'DrisBlackTwentyThree' has not been observed under all possible environmental conditions. The botanical description of 'DrisBlackTwentyThree' was taken from plants that were two to five years old. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary*, $2^{nd}$ edition by James G. Harris and Melinda Woolf Harris, unless where otherwise defined.

Classification:

*Family.*—Rosaceae.

*Botanical.*—*Rubus* L. subgenus *Rubus*.

*Common name.*—Blackberry.

*Variety name.*—'DrisBlackTwentyThree'.

Parentage:

*Female parent.*—'BN864.2' (unpatented).

*Male parent.*—'DrisBlackEighteen' (U.S. Plant Pat. No. 31,110).

Plant:

*Propagation.*—Root cuttings.

*Growth habit.*—Upright.

Canes:

*Fruiting lateral length* ($4^{th}$ *lateral from tip*).—78.7 cm.

*Number of fruits per fruiting lateral.*—16.5.

*Internodal distance.*—5.24 cm.

*Dormant cane.*—Anthocyanin color: RHS 183A (Dark red). Predominant distribution of branches: Over whole length. Cross-section: Round to angular. Presence of spines: Absent.

Young shoots:

*Anthocyanin color* (*during rapid growth*).—RHS 184A. (Greyish red).

*Intensity of green color.*—RHS 139D (Moderate yellow-green).

*Number of glandular hairs.*—Absent or few.

Leaves:

*Time of leaf bud burst.*—Medium.

*Terminal leaflet.*—Length: 117 mm. Width: 86 mm. Length/width ratio: 1.36. Lobing: Absent. Shape in cross-section: U-shaped. Undulation of margin: Weak.

*Lateral leaflets (basal pair).*—Length: 102 mm. Width: 71 mm. Length/width ratio: 1.44.

*Rachis length between terminal leaflet and adjacent lateral leaflets.*—12.1 mm.

*Rachis color.*—RHS 176C (Grayish reddish orange).

*Petiole.*—Length: 25 mm. Diameter: 2.5 mm. Color: RHS 176C (Grayish reddish orange).

*Stipule.*—Length: 8.7 mm. Shape: Caudate. Color: RHS 142C (Light yellowish green).

*Leaflet.*—Type of incision of margin: Bi-serrate. Depth of margin incisions: Medium. Apex shape: Convex. Base shape: Obtuse.

*Leaf.*—Predominant number of leaflets: 5 (although 3-leaflet leaves can appear on fruiting laterals). Type: Palmate. Glossiness of upper side: Medium. Intensity of green color of upper side: RHS 139A (Dark yellowish green). Color of lower side: RHS 141C (Strong yellowish green).

Flowers:

*Diameter.*—45.5 mm.

*Petal.*—Length: 23.9 mm. Width: 13.2 mm. Length/width ratio: 1.81. Color: RHS NN155C (White). Number of petals per flower: 5. Petal shape (overall): Oval. Apex shape: Rounded. Base shape: Attenuate.

*Sepal.*—Length: 11.1 mm. Width: 5.6 mm. Shape: Elliptic. Color of upper side: RHS 144B (Strong yellowish green). Color of lower side: RHS 141C (Strong yellowish green).

*Number of flowers observed at 3rd node from tip of lateral.*—1.7.

*Pedicel.*—Length: 52 mm. Diameter: 1 mm. Color: RHS 141C (Strong yellowish green).

*Stigma.*—Color: RHS 144D (Light yellowish green).

*Style.*—Color: RHS 144D (Light yellowish green).

*Filament.*—Color: RHS 157C (Pale yellowish green).

*Anther.*—Color: RHS 157B (Pale yellowish green).

*Pollen.*—Color: RHS 157B (Pale yellowish green).

*Time of beginning of flowering on previous year's cane.*—Medium.

Fruit:

*Length of mature fruit.*—31.3 mm.

*Diameter of mature fruit.*—24.2 mm.

*Ratio of length to width.*—1.29.

*Number of drupelets per fruit.*—Medium.

*Size of drupelets.*—Medium.

*Fruit shape in longitudinal section.*—Elliptic.

*Fruit color.*—RHS 203A (Black).

*Fruiting on current year's cane.*—Absent.

*Harvest interval on previous year's cane.*—June-August.

*Yield.*—29,000 to 36,000 pounds per acre of fruit per season from 24- to 36-month-old plants when grown in Watsonville, Calif.

*Market use of fruit.*—Fresh market.

Resistance to diseases:

*Fusarium wilt (Fusarium oxysporum).*—Resistant.

COMPARISONS TO PARENTAL AND COMMERCIAL BLACKBERRY VARIETIES

'DrisBlackTwentyThree' differs from the female parent 'BN864.2' (unpatented) in that 'DrisBlackTwentyThree' has higher yield potential compared to 'BN864.2'.

'DrisBlackTwentyThree' differs from the male parent 'DrisBlackEighteen' (U.S. Plant Pat. No. 31,110) in that 'DrisBlackTwentyThree' has an upright growth habit, a rounded to angular cross-section of dormant cane, medium anthocyanin coloration during rapid growth on young shoot, and a U-shape in cross-section of terminal leaflet, whereas 'DrisBlackEighteen' has an upright to semi-upright growth habit, an angular cross-section of dormant cane, weak anthocyanin coloration during rapid growth on young shoot, and a V-shape in cross-section of terminal leaflet. In addition, 'DrisBlackTwentyThree' has higher vigor than 'DrisBlackEighteen'.

'DrisBlackTwentyThree' differs from commercial blackberry variety 'DrisBlackSix' (U.S. Plant Pat. No. 25,502) in that 'DrisBlackTwentyThree' has an upright growth habit, medium anthocyanin coloration during rapid growth on young shoot, a white petal color, and an elliptic fruit shape in longitudinal section, whereas 'DrisBlackSix' has a semi-upright growth habit, strong anthocyanin coloration during rapid growth on young shoot, a white and pinkish petal color, and a narrow ovate fruit shape in longitudinal section.

'DrisBlackTwentyThree' differs from commercial blackberry variety 'DrisBlackThree' (U.S. Plant Pat. No. 23,725) in that 'DrisBlackTwentyThree' has an upright growth habit, a rounded to angular cross-section of dormant cane, spines absent on dormant cane, and an elliptic fruit shape in longitudinal section, whereas 'DrisBlackThree' has an upright to semi-upright growth habit, an angular cross-section of dormant cane, spines present on dormant cane, and an oblong fruit shape in longitudinal section.

What is claimed is:

1. A new and distinct variety of blackberry plant designated 'DrisBlackTwentyThree' as shown and described herein.

* * * * *